United States Patent [19]

Mills

[11] Patent Number: 5,455,021
[45] Date of Patent: Oct. 3, 1995

[54] ISOTOPIC TRACER COMPOSITION AND METHOD FOR MAKING AND USING SAME

[75] Inventor: Stanley L. Mills, Washington, Okla.

[73] Assignee: The Board of Regents of the University of Oklahoma, Norman, Okla.

[21] Appl. No.: 214,907

[22] Filed: Mar. 17, 1994

Related U.S. Application Data

[60] Continuation of Ser. No. 913,271, Jul. 14, 1992, abandoned, which is a division of Ser. No. 645,153, Jan. 22, 1991, Pat. No. 5,208,007, which is a division of Ser. No. 274,759, Nov. 22, 1988, abandoned.

[51] Int. Cl.$^6$ .......................... A61K 51/04; A61K 51/08; A61K 51/10
[52] U.S. Cl. .................. 424/141; 424/1.49; 424/1.57; 424/1.69; 424/1.45
[58] Field of Search .................... 424/1.41, 1.45, 424/1.49, 1.53, 1.57, 1.69; 530/391.3, 391.5

[56] References Cited

U.S. PATENT DOCUMENTS

| | | | |
|---|---|---|---|
| 4,057,617 | 11/1977 | Abramovici et al. | 424/1 |
| 4,272,503 | 6/1981 | Camin et al. | 424/1 |
| 4,418,052 | 11/1983 | Wong | 424/1.1 |
| 4,421,735 | 12/1983 | Haber et al. | 424/1.1 |
| 4,424,200 | 1/1984 | Crockford et al. | 424/1.1 |
| 4,460,561 | 7/1984 | Goldenberg | 424/1.1 |
| 5,164,175 | 11/1992 | Bremer et al. | 424/1.1 |
| 5,245,018 | 9/1993 | Kondo et al. | 534/14 |
| 5,268,163 | 12/1993 | Verbruggen | 424/1.1 |

*Primary Examiner*—Gary L. Geist
*Assistant Examiner*—Lara E. Chapman
*Attorney, Agent, or Firm*—Dunlap Codding

[57] ABSTRACT

An isotopic tracer composition and methods of making and using same for radiological evaluation of body functions and diseases in a subject and for radiological therapy. The isotopic tracer composition comprises a protein carrier agent such as fibrinogen, antibodies, enzymes or portions thereof, bound to a radioisotope which has been reduced to a lower oxidation state by stannous phosphate at a pH of greater than 7. Some suitable radioisotopes are isotopes of technetium, rhenium and ruthenium.

20 Claims, No Drawings

ISOTOPIC TRACER COMPOSITION AND METHOD FOR MAKING AND USING SAME

The present application is a continuation of U.S. Ser. No. 07/913,271, filed Jul. 14, 1992, now abandoned, which is a divisional of U.S. Ser. No. 07/645,153, filed Jan. 22, 1991, now U.S. Pat. No. 5,208,007, which is a divisional of U.S. Ser. No. 274,759, filed Nov. 22, 1988, now abandoned.

FIELD OF THE INVENTION

The present invention relates generally to isotopic tracer compositions used for radiological testing and treatment of subjects, and, more particularly, but not by way of limitation, relates to methods for producing and using a protein bound to rhenium, ruthenium or technetium.

DETAILED DESCRIPTION OF THE INVENTION

Isotopic tracer compositions are used in the diagnosis and treatment of disease states. Generally, an isotopic tracer composition comprises a carrier agent such as a protein or fragment thereof and a radioisotope. Once administered to a subject, the composition is directed to a targeted body component by the carrier agent which is bindingly specific to that targeted body component and is deposited thereon. If the radioisotope emits gamma radiation, an image of the targeted body component can be detected by a scintigraphic camera. From these emissions, the targeted body components can be evaluated; the presence of disorders such as tumors and blood clots can be detected and regulatory biological functions can be evaluated. If the radioisotope emits beta radiation, the targeted body component can be destroyed.

There have been many problems associated with the preparation of isotopic tracer compositions. One problem is a carrier agent such as a protein having functional sites which are not in a condition to bind to the radioisotope. The binding receptivity of the functional sites, which are any potential binding sites for the radioisotope, can be enhanced using the method of the present invention.

The functional site of a protein or fragment thereof can become bindingly receptive to a selected radioisotope when contacted with a sufficient quantity of an oxidizing agent for a sufficient amount of time thereby oxidizing the functional site. Oxidizing agents such as sodium metaperiodate or periodic acid can be added to the proteins by any method which allows the oxidizing agent to contact the functional site. Samples of the mixture may be taken at timed intervals and exposed to the radioisotope to determine when binding occurs.

Preferred proteins or fragments thereof utilized in accordance with the method of the present invention are fibrinogen which is directed to blood clots, and antibodies which are directed to tumors and enzymes which are directed to organ systems.

Since proteins are subject to damage, the oxidation reaction must be terminated prior to any substantial loss of intended biological activity of the proteins caused by damage to or changes in the configuration of the protein.

The termination of the oxidation reaction can be accomplished by removal or inactivation of the oxidizing agent. Preferably, the oxidizing agent is inactivated by contacting the oxidizing agent with an effective amount of an oxidation-terminating agent such as ethylene glycol which may be added to the protein-oxidation agent mixture in any effective amount. Generally, the optimum time to terminate the oxidation reaction is as soon as a substantial amount of the proteins will bind to the radioisotope.

The selected radioisotopes for use with the method of the present invention comprise the isotopes of Rhenium such as Re-186 and Re-188, Ruthenium such as Ru-97 and Technetium such as Tc- 99m. However, other radioisotopes may be used that bindingly respond to proteins and protein fragments treated with the method of the present invention.

Besides the binding receptivity of the protein, there have been other problems associated with binding proteins to radioisotopes which require a reduction process. Reduction conditions can be harsh which can damage the protein. For example, when technetium-99m comes from the generator, it is in the form of $^{99m}TCO_{4-}$ and requires reduction of the oxidation state to 3+ or 4+ in order to be in a condition which can bind a protein. If the conditions of the reduction are too harsh or stringent e.g., an acidic pH, the proteins will be damaged. This damage can result in poor binding of the protein, unattached radioisotope, excessive degradation products which require purification, and colloidal formation. The method of the present invention protects the protein from substantial harm thereby generally avoiding the purification step and other associated problems.

Accordingly, the present invention comprises a method for preparing an isotopic tracer composition comprising a protein or fragment thereof and a radioisotope characterized by the ability to bind a protein or fragment thereof when reduced to a lower oxidation state by a sufficient amount of stannous phosphate. Preferably, these radioisotopes are isotopes of Technetium such as Tc-99m, Rhenium such as Re-186 and Re-188, and Ruthenium such as Ru-97. The radioisotope is present in an amount to effectively bind the quantity of protein or protein fragment needed for the intended application of the isotopic tracer composition. The quantity of the radioisotope and the protein or protein fragment can be determined according to NM/MIRD, Pamphlet nos. 10 & 11, Society of Nuclear Medicine (New York, N.Y. 1975). Preferably, the proteins utilized in the present invention are fibrinogen, antibodies, enzymes or fragments thereof.

The radioisotope is contacted by an amount of stannous phosphate capable of reducing at least a substantial amount of the radioisotope to a lower oxidation state in order to bind to the protein or protein fragment. This reduction process occurs at a pH of greater than 7. The pH may be adjusted by adding a sufficient amount of an alkalizing agent to the composition such as sodium hydroxide, borate buffer or bicarbonate buffer. The amount of the alkalizing agent will depend upon the original pH of the solution, the volume of the solution and the components in the solution.

After the radioisotope is reduced to an oxidation state which renders the radioisotope capable of binding the protein or protein fragment, the protein or protein fragment is exposed to the reduced radioisotope at a pH greater than 7 thereby binding the protein or protein fragment. The protein is exposed to the reduced radioisotope in any manner which permits binding of an effective amount of protein or protein fragment without substantial damage to the protein.

In a preferred embodiment the protein is in a solution to which is added the sodium hydroxide, technetium-99m, and stannous phosphate, in that order, so that the reduction of the radioisotope and the binding of the protein to the radioisotope occurs in the same container. The order of mixing the protein, the radioisotope, the stannous phosphate and the alkalizing agent is not crucial except that the protein must be protected from an acidic pH. A sufficient amount of time is required to permit the binding of a substantial amount of protein to the radioisotope prior to administration. Generally, this is between five and thirty minutes.

The isotopic tracer composition is preferably injected intravenously into a subject such as a human. In order to prevent discomfort to the subject the composition may be buffered to about a physiological pH which is about 7. Again, five to thirty minutes should be allowed before the addition of the buffer. Any effective amount of a buffering agent may be used which does not adversely effect the intended activity of the isotopic tracer composition such as phosphate buffer, borate buffer, citrate buffer, ascorbic acid or hydrochloric acid.

Additionally, since chelating agents have been utilized to enhance the site specificity of a carrier agent [see L. DeRiemer, et al., *Journal of Medicinal Chemistry*, 22(9): 1019–1023 (1979)] the method of the present invention may further comprise binding a chelating agent to at least a portion of the proteins or protein fragments. The chelating agent is bound first to the protein or protein fragment before exposure to the reduced radioisotope. The chelating agent binds to a substantial amount of the proteins or protein fragments in a manner that permits the protein to function as intended. Preferably, the amount of chelating agent used is proportionally equivalent to the amount of protein used, i.e., one chelating agent for each protein or protein fragment. One example of a chelating agent is EDTA.

The present invention also comprises an isotopic tracer composition comprising proteins or fragments thereof in either a scintigraphically observable amount or an amount required to deposit a beta emitting radioisotope at a biosite for treatment thereof. In a preferred embodiment, the proteins are fibrinogen, antibodies, enzymes or fragments thereof. A radioisotope is bound to the protein or protein fragment which is present in any quantity sufficient to bind to at least a substantial amount the proteins or protein fragments. Determination of amounts of the proteins and the radioisotopes utilized in accordance with the present invention can be determined by the NM/MIRD, Pamphlet nos. 10 & 11, Society of Nuclear Medicine (New York, N.Y. 1975).

The radioisotope is selected from those radioisotopes which can be treated with a sufficient amount of stannous phosphate in order to produce a condition in the radioisotope which is bindingly receptive to the protein or protein fragment; this condition is a reduction in the oxidation state. The preferred radioisotopes of the present invention are isotopes of Technetium such as Tc-99m, isotopes of Rhenium such as Re-186 and Re-188 and isotopes of Ruthenium such as Ru-97.

During this binding process, the proteins have been protected from substantial damage, as previously described, due to the presence of an alkalizing agent producing a pH of greater than 7. Some pH ranges which can provide better protection for the protein may be utilized in the present invention. Therefore, preferably the pH is 9–12, and most preferably, 9–10 which is an extremely hospitable pH for the proteins. Some suitable alkalizing agents to adjust the pH are sodium hydroxide, borate buffer and bicarbonate buffer.

The composition also comprises stannous phosphate, a reducing agent, which reduces the radioisotope to a lower oxidation state at a pH which is not damaging to the proteins. The stannous phosphate is present in the composition in any amount which permits this reduction of the radioisotope.

The composition of the present invention may further comprise an effective amount of a chelating agent capable of binding to at least a substantial amount of the proteins. The chelating agent is disposed in proximity to the protein so that binding of the chelating agent to the protein occurs. This binding process occurs before the protein is exposed to the radioisotope. Any unbound chelating agent is removed to prevent binding of the radioisotope to the unbound chelating agent; this may be accomplished by standard purification procedures such as gel chromatography or affinity chromatography.

In a preferred embodiment, a solution containing EDTA, capable of binding to a protein or a protein fragment, is added to a vial containing fibrinogen prepared by the method of *Arkiv Kemi* 10: 415–444 (1956). The contents of the vial is swirled and allowed to incubate until a substantial amount of the fibrinogen is chelated to the EDTA. After purification to remove unbound EDTA, the resulting solution then is exposed to the reduced technetium-99m, as previously described.

If needed, a pharmaceutically acceptable carrier may be added to the composition in order to more easily administer the composition to a subject. The carrier should be sterile and not interfere with the intended activity of the components disposed therein. Preferably, the pharmaceutically acceptable carrier is also isotonic to prevent discomfort to the subject upon injection. Examples of pharmaceutically acceptable carriers are Sterile Normal Saline and Sterile Dextrose 5% in Water, or combinations thereof.

A buffering agent in an amount to produce about a physiological pH may also be added to the composition so as not to cause discomfort to the subject upon administration. Some suitable buffering agents are phosphate buffers, borate buffers, citrate buffers, ascorbic acid and hydrochloric acid.

In a preferred embodiment, the composition of the present invention comprises 100 µg of Lym-1 produced by Lederle, Pearl River, N.Y., which is a monoclonal antibody against human B-cell lymphoma; 25 µl of 0.02M borate buffer, pH 9.0; 500 µCi of technetium-99m; 380 µg stannous phosphate; and 0.1M phosphate buffer, pH 7.0; and 1 ml of Sterile Normal Saline.

The composition of the present invention generally requires no purification process prior to administration due to the significant degree of labeling of the protein or protein fragment and absence of significant degradation products and colloidal formations.

It may be appreciated from the foregoing that the composition of the present invention has been simplified to the point that a nuclear pharmacist on-site at an institution such as a hospital could prepare the composition of the present invention if the appropriate materials were available. Accordingly, the present invention comprises a kit for making a reagent to be used with an effective amount of radioisotope and a bindingly receptive protein or protein fragment to produce an isotopic tracer composition.

The kit of the present invention comprises an effective amount of an alkalizing agent capable of producing a pH of greater than 7 in the isotopic tracer composition; and an effective amount of stannous phosphate capable of reducing an effective amount the radioisotope to a lower oxidation state capable of binding the protein or protein fragment. The kit may also comprise a bindingly receptive protein or protein fragment such as fibrinogen, antibodies, enzymes, or fragments thereof or the protein may be obtained from another source in an amount effective for the intended purpose as calculated by the method of NM/MIRD Pamphlets Nos. 10–11, Society of Nuclear Medicine (New York, N.Y., 1975).

The alkalizing agent produces a pH of greater than 7, more preferably, a pH of 9–12, and, most preferably, a pH of 9–10. The previously described alkalizing agents may be used.

The components of the kit of the present invention are preferably packaged individually in sterile containers such as vials or syringes. Several components of the kit may be packaged in one container if the components will not be damaged, and if the resulting mixture is stable enough to permit the intended activity of each component as previously described.

In a preferred embodiment, a kit of the present invention comprises a vial containing fibrinogen and sodium hydroxide as an alkalizing agent; syringe A contains stannous phosphate; and syringe B contains hydrochloric acid as a buffer.

The components of the present invention are mixed in an order to prevent damage to the protein. A preferred order of mixing is to first combine the protein with the alkalizing agent. The radioisotope, which is preferably provided by a source outside the kit, is then added to the mixture of protein and alkalizing agent. To this is added the stannous phosphate. The order of mixing the radioisotope, protein, stannous phosphate and alkalizing agent is not crucial except that the protein must be protected from an acidic pH.

If the pH of the resulting solution of the kit would wake intravenous injection uncomfortable to the recipient subject, the kit way further comprise an effective amount of a buffering agent capable of producing about a physiological pH. The buffering agent can interfere with the binding of the radioisotope to the protein; therefore, the buffering agent is packaged in a separate aseptic container. A chelating agent as previously described, either bound to the protein or in a separate container may be added to the kit.

Due to the nature of the radioisotope, it is preferably that the radioisotope be provided separate from the kit. However, if feasible, the kit could include the radioisotope.

The reagent prepared by the kit is for use with a radioisotope capable of binding a bindingly receptive protein or protein fragment when the radioisotope is reduced to a lower oxidation state by a sufficient amount of stannous phosphate, as previously described. Examples of this type of radioisotope are isotopes of Technetium such as Tc-99w, Rhenium such as Re-188 and Re-186, and Ruthenium such as Ru-97.

Once the isotopic tracer composition has been prepared, it may be administered to a subject by intravenous injection and observed scintigraphically. Accordingly, the present invention comprises a method for labeling a targeted body component of a subject, preferably a human, by directing a scintigraphically observable radioisotope contained in a composition to a targeted area in a subject. As previously described, the composition comprises a protein bound to the radioisotope, stannous phosphate and an alkalizing agent. The composition of the present invention may further comprise a buffering agent and/or a chelating agent, as previously described.

The radioisotope of the composition is reduced to a lower oxidation state by stannous phosphate to be bindingly receptive to the protein as previously described. Some suitable radioisotopes are isotopes of Technetium such as Tc-99m, Rhenium such as Re-188 and Re-186, and Ruthenium such as Ru-97.

Once administered, the protein or protein fragment is directed to a body component for which it is bindingly specific. The body component on which the composition has been deposited will be scintigraphically observable thereby effectively labeling the targeted body component. Preferably, the protein is fibrinogen, an enzyme, an antibody or a fragment thereof.

The subject is preferably administered the solution described above by intravenous injection by a slow intravenous push over a period of several minutes. Purification of the solution is not necessary due to the almost complete binding of the protein by the radioisotope and the lack of significantly harmful degradation products. Following administration of the isotopic tracer solution, the subject preferably is place before a scintigraphic camera to detect the gamma radiation emitted from the target area.

The following examples illustrate the practice of the present invention:

EXAMPLE ONE

In the event that a carrier molecule such as a protein does not bind to a radioisotope, this method may be followed to enhance labeling efficiency. The procedure may be modified for each type of material.

Oxidation may be carried out in 0.05M sodium acetate buffer at pH 4.5 and 4 degrees in the dark. The concentration of the material to be oxidized should be approximately 5 mg/ml and a concentration of sodium metaperiodate or periodic acid varying from 0.01M to 0.08M may be used. Experiments at two separate concentrations of periodate should be performed to ensure that no significant differences due to the limitation of periodate are encountered. Aliquots may be taken at several times up to 48 or 72 hours for various analysis. These should be taken more frequently during the early period of the oxidation procedure. The reaction is terminated with an excess of ethylene glycol. The material is then purified by dialysis, gel chromatography, or centrifuge column chromatography. The specific procedure is sodium acetate buffer 0.05M, pH 5.5, and periodic acid 0.015M final concentration.

Termination of oxidation should be done before any loss of immunoreactivity or major conformational changes are made in the material. The object is to produce reactive sites on the protein which will bind the specific radioisotope.

EXAMPLE TWO

If stannous phosphate is not commercially available, it can be prepared by combining 8.1 gm sodium phosphate dibasic with 190.1 mg of stannous chloride anhydrous and a sufficient quantity of Sterile Water for Injection, USP to make 100 ml. Nitrogen gas is forced through a 0.2 micron filter and bubbled through the solution for 30 minutes before use.

EXAMPLE THREE

To one hundred µg of Lym-1 in an aqueous solution of 25 µl is added 25 µl of 0.02M borate buffer, pH 9.0; 500 µCi of technetium-99m in 150 µl of generator elution; and 380 µg of stannous phosphate. The mixture is allowed to incubate for 30 minutes at room temperature. One ml of 0.1M phosphate buffer, pH 7 is added thereto. The final pH was 7.3.

The binding yield at 30 minutes was 100% technetium-99m binded Lyre-1 as shown by high pressure liquid chromatography, using TSK-3000 column and 0.1M phosphate buffer, pH 7.0 eluted at one ml per minute.

EXAMPLE FOUR

One example of the kit of the present invention is as follows:

(1) Vial containing 10–20mg PURIFIED HUMAN FIBRINOGEN and 0.1–0.5 ml of 1 N Sodium Hydroxide to make a pH of 9–10.

(2) Syringe A containing 0.2 ml of stannous phosphate made from in the following manner: 8.1 gm of Sodium Phosphate Dibasic and 190.1 mg of Stannous Chloride Anhydrous dissolved in a sufficient quantity of Sterile Water for Injection, USP to make 100 ml. Nitrogen gas is forced through a 0.2 micron filter and bubbled through the Sterile Water for 30 minutes before use.

(3) Syringe B containing 0.1–0.5 ml of 1 N Hydrochloric Acid. The volume used is dependent upon quantity of fibrinogen and sodium hydroxide in vial.

Ten (10) µCi of technetium-99m is added to the vial. The vial is swirled to dissolve the contents. The contents of syringe A is added to the vial and incubated for five to thirty minutes. The contents of syringe B is then added to the vial. The solution in the vial in injected intravenously into a mammal and the standard scintigraphic procedure followed.

This kit produced technetium-99m binded fibrinogen at a pH of 7–8 with greater than 90% radioactivity of the fibrinogen as shown by cellulose acetate electrophoresis. This isotopic tracer may be used to detect deep vein thrombosis.

Changes may be made in the steps or the sequence of steps of the methods described herein or in the binding composition or the elements of the binding compositions described herein or in the kit or in the components of the kit described herein without departing from the spirit and scope of the invention as defined in the following claims.

What is claimed is:

1. A method for preparing an isotopic tracer composition comprising a protein or fragment thereof and a radioisotope characterized by the ability to bind a protein or fragment thereof when treated with a sufficient amount of stannous phosphate, consisting of the steps of:

contacting an effective amount of the radioisotope with an amount of stannous phosphate which is sufficient to reduce a substantial amount of the radioisotope to a lower oxidation state at a pH greater than 7; and exposing an effective amount of the protein or fragment thereof to the reduced radioisotope at a pH of 9–12 thereby binding the protein or fragment thereof to the radioisotope.

2. The method of claim 1 wherein the protein is selected from the group consisting of fibrinogen, antibodies, and enzymes.

3. The method of claim 1 wherein the radioisotope is an isotope selected from the group consisting of Rhenium, Ruthenium and Technetium.

4. The method of claim 3 wherein the group consisting of Rhenium, Ruthenium and Technetium includes Re-188, Re-186, Ru- 97, and Tc-99m.

5. The method of claim 1 wherein in the exposing step the pH for binding the protein is 9–10.

6. A method for preparing an isotopic tracer composition comprising a protein or fragment thereof and a radioisotope characterized by the ability to bind a protein or fragment thereof when treated with a sufficient amount of stannous phosphate, consisting of the steps of:

contacting an effective amount of the radioisotope with an amount of stannous phosphate which is sufficient to reduce a substantial amount of the radioisotope to a lower oxidation state at a pH greater than 7;

exposing an effective amount of the protein or fragment thereof to the reduced radioisotope at a pH of 9–12 thereby binding the protein or fragment thereof to the radioisotope; and buffering the isotopic tracer composition to about a physiological pH.

7. The method of claim 6 wherein the protein is selected from the group consisting of fibrinogen, antibodies, and enzymes.

8. The method of claim 6 wherein the radioisotope is an isotope selected from the group consisting of Rhenium, Ruthenium and Technetium.

9. The method of claim 8 wherein the group consisting of Rhenium, Ruthenium and Technetium includes Re-188, Re-186, Ru- 97, and Tc-99m.

10. The method of claim 6 wherein in the exposing step the pH for binding the protein is 9–10.

11. A method for preparing an isotopic tracer composition comprising a protein or fragment thereof and a radioisotope characterized by the ability to bind a protein or fragment thereof when treated with a sufficient amount of stannous phosphate, consisting of the steps of:

contacting an effective amount of the radioisotope with an amount of stannous phosphate which is sufficient to reduce a substantial amount of the radioisotope to a lower oxidation state at a pH greater than 7;

binding a chelating agent to at least a portion of the protein or fragment thereof; and exposing an effective amount of the protein or fragment thereof to the reduced radioisotope at a pH of 9–12 thereby binding the protein or fragment thereof to the radioisotope.

12. The method of claim 11 wherein the radioisotope is an isotope selected from the group consisting of Rhenium, Ruthenium and Technetium.

13. The method of claim 12 wherein the group consisting of Rhenium, Ruthenium and Technetium includes Re-188, Re-186, Ru-97 and Tc-99m.

14. The method of claim 11 wherein the protein is selected from the group consisting of fibrinogen, antibodies, and enzymes.

15. The method of claim 11 wherein in the exposing step the pH for binding the protein is 9–10.

16. A method for preparing an isotopic tracer composition comprising a protein or fragment thereof and a radioisotope characterized by the ability to bind a protein or fragment thereof when treated with a sufficient amount of stannous phosphate, consisting of the steps of:

contacting an effective amount of the radioisotope with an amount of stannous phosphate which is sufficient to reduce a substantial amount of the radioisotope to a lower oxidation state at a pH greater than 7;

binding a chelating agent to at least a portion of the protein or fragment thereof;

exposing an effective amount of the protein or fragment thereof to the reduced radioisotope at a pH of 9–12 thereby binding the protein or fragment thereof to the radioisotope; and buffering the isotopic tracer composition to about a physiological pH.

17. The method of claim 16 wherein the radioisotope is an isotope selected from the group consisting of Rhenium, Ruthenium and Technetium.

18. The method of claim 17 wherein the group consisting of Rhenium, Ruthenium and Technetium includes Re-188, Re-186, Ru- 97, and Tc-99m.

19. The method of claim 16 wherein the protein is selected from the group consisting of fibrinogen, antibodies, and enzymes.

20. The method of claim 16 wherein in the exposing step the pH for binding the protein is 9–10.

* * * * *